United States Patent [19]

Meller et al.

[11] Patent Number: 5,219,285

[45] Date of Patent: * Jun. 15, 1993

[54] DISPOSABLE RIGHT ANGLE DENTAL HANDPIECE

[75] Inventors: Moshe Meller, Lakewood; Michael Feldman, Howell, both of N.J.

[73] Assignee: MTI Precision Products, Inc., Lakewood, N.J.

[*] Notice: The portion of the term of this patent subsequent to Apr. 16, 2008 has been disclaimed.

[21] Appl. No.: 663,401

[22] Filed: Mar. 1, 1991

Related U.S. Application Data

[63] Continuation-in-part of Ser. No. 502,454, Mar. 30, 1990, Pat. No. 5,007,832.

[51] Int. Cl.⁵ ............................................. A61C 1/08
[52] U.S. Cl. ................................... 433/126; 433/125
[58] Field of Search ............... 433/114, 116, 125, 126, 433/127, 128, 129, 133

[56] References Cited

U.S. PATENT DOCUMENTS

| | | | |
|---|---|---|---|
| 1,982,336 | 11/1934 | Wiseman | 433/125 |
| 3,163,934 | 1/1965 | Wiseman | 433/125 |
| 3,727,313 | 4/1973 | Graham | 433/125 |
| 3,798,777 | 3/1974 | Reifer | 433/125 |
| 3,835,858 | 9/1974 | Hagen | 433/126 |
| 4,123,845 | 11/1978 | Fattaleh | 433/126 |
| 4,211,009 | 7/1980 | Leonard | 433/126 |
| 4,245,985 | 1/1981 | Eibofner et al. | 433/126 |
| 4,310,310 | 1/1982 | Bailey | 433/126 |
| 4,365,956 | 12/1982 | Bailey | 433/125 |
| 4,449,932 | 5/1984 | Lustig | 433/126 |
| 4,544,356 | 10/1985 | Gardella et al. | 433/125 |
| 4,604,058 | 8/1986 | Fisher et al. | 433/125 |
| 5,020,994 | 6/1991 | Huang | 433/126 |

FOREIGN PATENT DOCUMENTS

| | | | |
|---|---|---|---|
| 508696 | 4/1928 | Fed. Rep. of Germany | 433/126 |
| 3227417 | 2/1983 | Fed. Rep. of Germany | 433/126 |
| 2584918 | 1/1987 | France | 433/126 |

Primary Examiner—Cary E. O'Connor
Attorney, Agent, or Firm—Frishauf, Holtz, Goodman & Woodward

[57] ABSTRACT

A disposable right angle dental handpiece comprises a disposable plastic outer housing having an elongated opening therein for receiving a drive shaft mechanism which is preferably made of metal. The drive shaft mechanism is connected to the disposable outer plastic housing by means of a quick connect-quick disconnect mechanism. The outer housing also contains a gear which is engaged with a gear at the end of the drive shaft mechanism, a working member being connected to the gear for being driven by the drive shaft member. The drive shaft member is connectable to the dental tool for being driven thereby. Also disclosed are embodiments wherein the drive shaft mechanism is connected to the dental drive tool, and wherein the outer housing is independently connected to the dental drive tool by means of a quick connect-quick disconnect mechanism, which locks the outer housing relative to the dental drive tool in both the longitudinal and circumferential directions.

12 Claims, 7 Drawing Sheets

DISPOSABLE RIGHT ANGLE DENTAL HANDPIECE

RELATED APPLICATION

This application is a continuation-in-part of our co-pending application Ser. No. 07/502,454, filed Mar. 30, 1990, now U.S. Pat. No. 5,007,832.

BACKGROUND OF THE INVENTION

This invention relates to a disposable dental handpiece, and more particularly to a disposable right angle dental prophylaxis handpiece.

Disposable dental prophylaxis right angle hand pieces are known, for example, from U.S. Pat. No. 3,727,313, the entire contents of which are incorporated herein by reference. Such disposable dental handpieces are desirable since the portions that come into contact with a patient may be thrown away after use, thereby eliminating the expense of sterilizing the handpiece and also eliminating the risk of incomplete sterilization and/or transfer of infection. At present, the transfer of infection is of utmost concern.

The disposable right angle hand piece of U.S. Pat. No. 3,727,313 is disadvantageous in that all of the internal parts thereof are made of disposable plastic materials, and thus the device provides poor operability. The shaft itself is made of plastic and provide poor engagement with the drive mechanism. Moreover, plastic particles wear off the shaft and cause damage to the drive mechanism of the dental equipment. The plastic gears are inferior and provide poor power transmission between the drive shaft and the elastic rubber working cup 24. Also, the plastic gears tend to wear during use, even for a short time.

The object of the present invention is to provide an improved disposable right angle prophylaxis hand-pieces which has improved operability, which overcomes the disadvantages inherent in the design of known devices such as that disclosed in U.S. Pat. No. 3,727,313.

SUMMARY OF THE INVENTION

According to the present invention, a disposable right angle handpiece comprises an outer housing made of disposable plastic material and having an elongated opening therein for receiving a drive shaft means; a cavity in said housing for receiving a driven member; means coupling a working member to said driven member for performing a working operation in an oral cavity of a patient; and a drive shaft means, preferably made of metal, receivable in said elongated opening of said outer housing and having means at one end thereof for engaging with a dental drive means of a dental tool, and being rotatable within said housing, and having a driving member at the distal end thereof which engages with said driven member so as to rotatably drive said driven member. Means is provided for removably coupling said drive shaft means to the dental drive means, and for removably coupling the outer housing to the dental drive means with drive shaft means in said housing, and for permitting disengagement of said housing from said drive shaft means and said dental drive means for disposal of said housing.

DETAILED DESCRIPTION

Figures 1, 2:
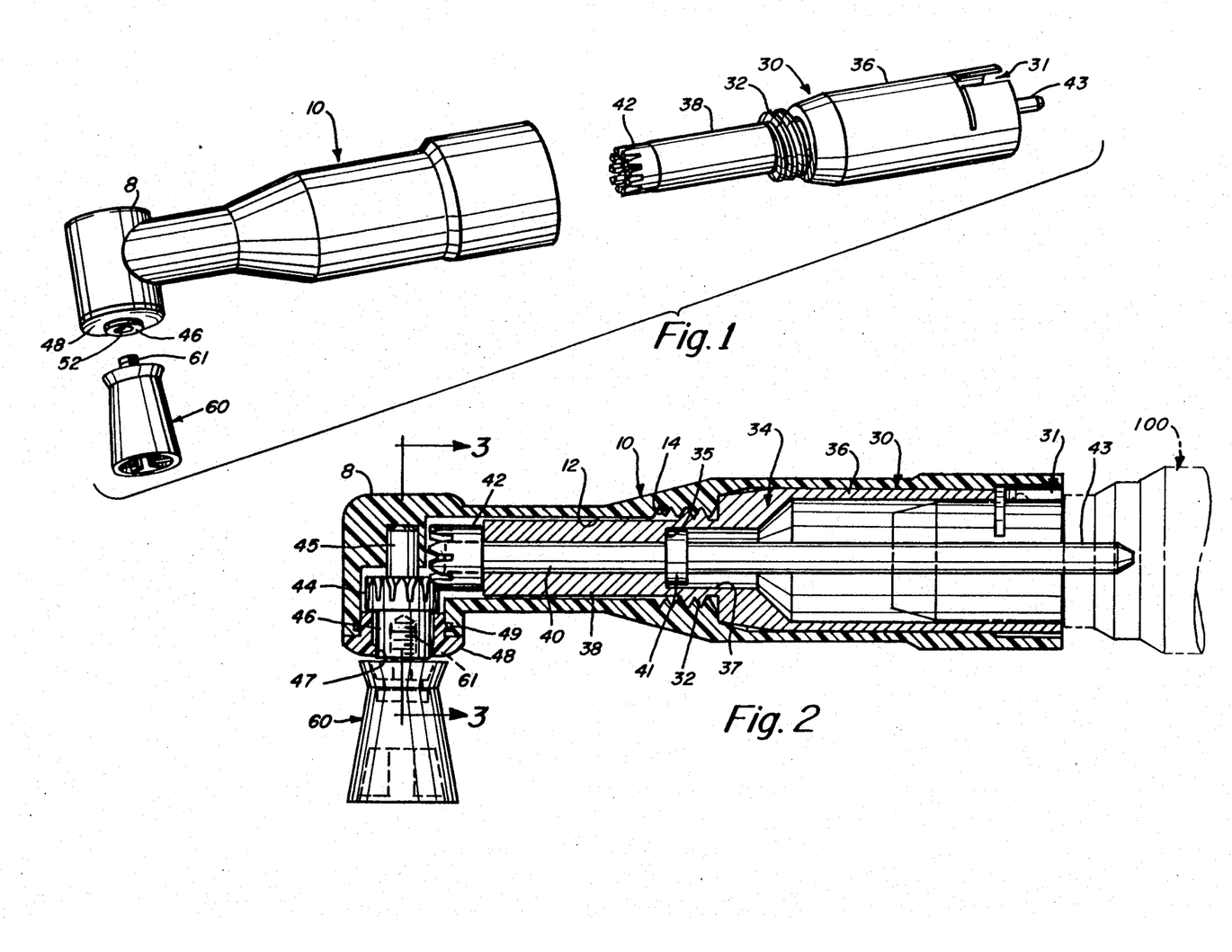
FIG. 1 is a disassembled perspective view of a disposable right angle dental handpiece according to the present invention.
FIG. 2 is a longitudinal cross-sectional view thereof in the assembled state.

Referring to FIGS. 1 and 2, the right angle dental handpiece of the present invention comprises a hollow outer housing 10 which has an elongated opening therein for receiving a drive member 30 therein. A working member, for example, a conventional elastic rubber cup 60, is connected to the distal end of the housing 10 so as to be rotated via a gear arrangement by means of the drive member 30. The outer housing 10 is preferably made of plastic material and is disposable. The drive member 30 is preferably made of metallic material, such as brass, so that it can be re used or disposed of after each use. The design of the drive member 30 is relatively simple and inexpensive to manufacture. Therefore, even if it is disposed of often, the design is still economical.

Figures 3, 4:
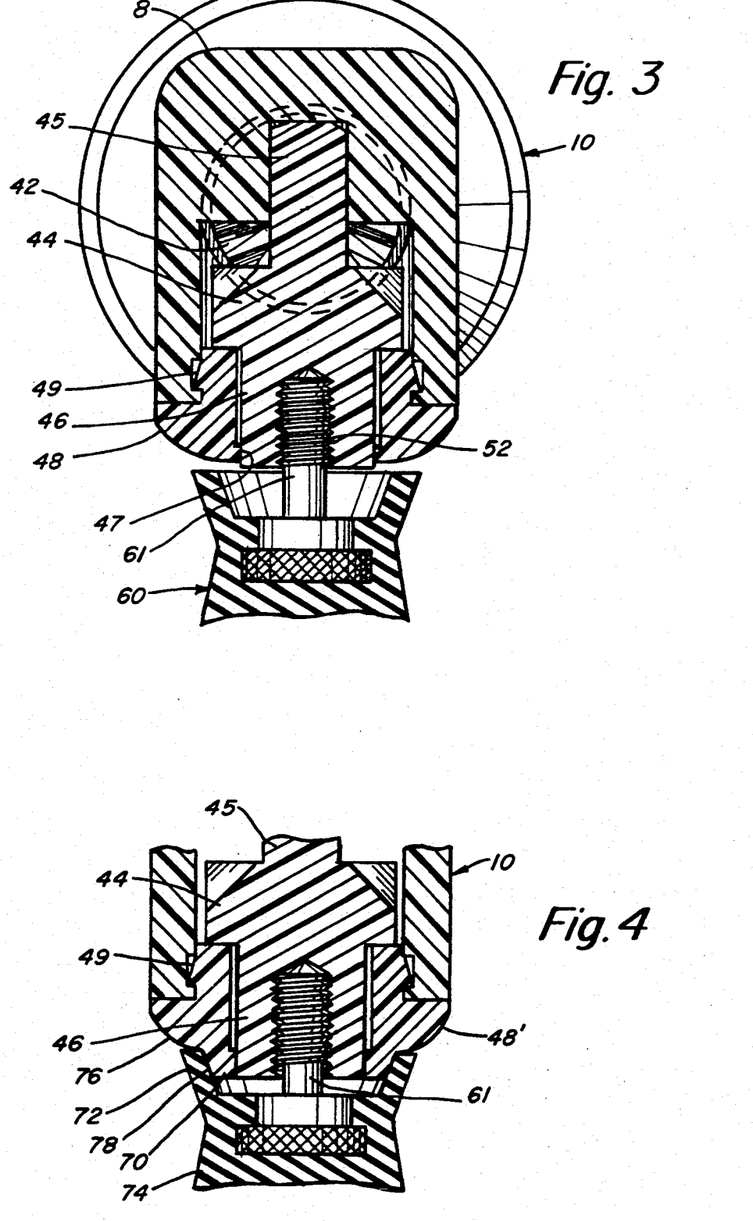
FIG. 3 is a cross-sectional view thereof taken along line 3—3 in FIG. 2.
FIG. 4 is a cross-sectional view similar to FIG. 3, but illustrating a modified arrangement of the present invention.

Referring to FIGS. 2 and 3, the outer plastic housing 10 has an inner elongated opening 12 formed therein for receiving the drive member 30. The drive member 30 has a threaded portion 32 which threadably engages a threaded portion 14 of housing 10. The drive member 30 comprises an outer housing portion 34 which comprises a larger diameter portion 36 and a smaller diameter portion 38 which are integrally formed with the threaded portion 32 interposed therebetween. A shaft 40 extends through said drive member housing 34 and has a bearing 41 at an intermediate portion thereof for rotatably engaging an inner surface 37 of the housing and for engaging an end-stop surface 35 of the housing 34 to limit the forward axial movement of the shaft 40. The bearing 41 serves as a sleeve-type bearing with the inner surface portion 37 of the housing 34. The contact portions between said shaft 40 and housing portion 36, 38 may also be considered as sleeve-type bearings which rotatably support shaft 40.

A gear 42 is fixed (i.e., press fit) to the distal end of shaft 40 for driving the cup 60, as will be explained hereinbelow. The gear 42 engages a forward wall of the small diameter portion 38 to act as a stop mechanism to prevent rearward movement of the shaft 40 relative to the housing 34. The gear 42 preferably has a hole therein which is press fit over the forward extending end of shaft 40. The opposite or proximal end of the shaft 40 extends outwardly rearwardly of the housing 30 and engages the dental drill or dental tool handpiece 100 so as to be rotated by a motor or other drive means connected thereto, in a conventional manner. The end 43 of the shaft 40 is connected to the drill tool 100 in a conventional manner, for example by means of a chuck or the like, in the same manner as in U.S. Pat. No. 3,727,313. Housing 30 has a T-shaped slit or opening 31 formed therein for engagement with a conventional locking device of a dental hand tool 100 to secure the handpiece of the present invention onto the dental tool 100. A detailed explanation of this locking device is unnecessary, since it is conventional. Other types of connecting mechanisms or units other than as shown in FIG. 2 can be used. Shaft end 43 would be modified accordingly, as would opening 31, to fit the desired connecting apparatus at the drive end of the dental tool handpiece.

The distal or head end of the housing 10 defines a cavity containing a rotatable gear 44 which meshes with gear 42 so as to be rotated thereby. The gear 44 is preferably made of metal, but could be made of plastic material, and has a shaft 45 extending upwardly therefrom for rotation within a bearing opening in the distal or head end of the housing 10. The opposite end 46 of the gear 44 rotates against a bearing surface 47 of the cap 48 of the housing 10. The cap 48 is preferably press fit into an opening in the distal end of the housing 10 and has a circumferential protrusion 49 thereon for snap-type engagement into a corresponding circumferential groove in the head end of the housing 10. Alternatively, the projection 49 can be provided on the inner surface of the opening adjacent the cap 48, and the cap 48 can be provided with a circumferential groove thereon for receiving the projection to lock the cap 48 on the housing. This arrangement provides an effective seal for preventing contamination from entering into the interior of the housing 10 and prevents wearing of the gears, shafts and bearings within the housing 10.

The flexible cup 60 preferably has a threaded shaft 61 (preferably metal, but it could be plastic) extending therefrom which is threadably inserted into a threaded opening 52 in gear member 46 so that upon rotation of the gear 46, the cup is similarly rotated. The direction of threads is such as to tighten the thread engagement during rotation of the cup by the shaft 40.

The contact area at the surface portion 47 and the gear 46 is sufficiently close (i.e., the clearance therebetween is sufficiently small) that contamination is effectively prevented from entering within the interior of the housing 10. However, in order to improve the seal between the distal end of the housing and the working member 60, the housing can be modified as shown in FIG. 4 by forming a downward projection 70 at the distal end of the housing (on cap 48') and by forming an upward projection 72 on the flexible cup 74. The upper tip end of the upward projection 72 of the cup 74 is dimensioned so as to be very close to the upper wall 76 of the distal end of the housing 10. Also, an elongated surface sliding contact area is provided between the upper projection 72 of the cup 74 and the outer surface portion of housing projection 70, as shown at 78 in FIG. 4. The upwardly extending portion 72 of the cup 74 is resilient, thereby improving the seal between the downward projection 70 of the housing and the upwardly projecting portion 72, thereby further preventing entry of contamination into the interior of the housing.

In use, the assembled dental tool of the present invention (for example, as assembled in FIG. 2) is mounted on the end of a conventional dental tool handpiece 100 (see FIG. 2) and is locked thereon by means of the engagement opening 31. The end 43 of the shaft 40 is engaged in the chuck of the dental tool 100 in a conventional manner. As mentioned above, other types of interconnecting techniques between the shaft 40 and the dental tool 100 can be provided, depending upon the construction of the particular dental tool handpiece 100 with which the device of the present invention is used. As required, the device of the present invention is fabricated with different types of dental tool connecting means, and is not limited to the particular construction shown in the present drawings.

After the device of the present invention is mounted on the dental tool handpiece 10, it is used in the normal manner by the practitioner. After use, the outer housing and the working cup 60 can be easily removed, for example, by twisting off the outer housing 10 from the drive shaft mechanism 30. The threads 32, 37 are of a quick connect-quick disconnect type, meaning that they are preferably designed so that only a half turn or three quarters of a turn thereof will disengage the outer housing 10 from the drive shaft portion 30. The device is preferably disassembled while it is still connected to the dental tool 100 so that the dental tool 100 anchors the drive shaft member 30 in place, and the housing 10 is more easily removed therefrom. Still further, the head end of the right angle dental handpiece of the present invention, and the projecting cup 60, provides convenient gripping and leverage producing areas to facilitate turning of the outer housing 10 for removal thereof. The outer housing 10, with its internal gear 46, along with the working cup 60 can then be readily disposed of, leaving only the metallic drive shaft portion 30 connected to the drill 100. Since contamination is effectively prevented from entering into the interior of the housing 10, the drive shaft portion 30, being made of metal, can be reused. If desired, or if contamination has inadvertently entered the interior of the housing 10, the drive shaft mechanism 30 can be sterilized for reuse in an easy manner.

Since the internal drive shaft portion 30 is made of metal, and has extremely good durability and operability, the device of the present invention provides the advantages of low cost disposability while also providing excellent operability of the device without the problems inherent in the all plastic disposable devices of the type disclosed in U.S. Pat. No. 3,727,313.

While the threads 32, 37 are shown as providing the interconnection between the drive mechanism 30 and the outer housing 10, various other quick connect-quick disconnect mechanism could be used, such as a bayonet connection, snap-type connection, ball and socket-type connection, or the like, could be used. The threaded portions are shown by way of example and is not limiting of the present inventive concept.

The other disposable housing 10 of the present invention is made of an FDA approved plastic material, such as nylon No. 6/6. However, other FDA approved plastic materials which are low in cost and sufficiently rugged can be used. The drive shaft means including the housing 34 and drive shaft 40 are preferably made of metal material such as brass, brass coated with chrome, brass coated with nickel, or other suitable metallic materials. The gears 42, 44 are preferably mode of stainless steel or other hard metal material, but could also be made of brass, brass coated with chrome or nickel, or the like. The shaft 45 of gear 44 may also be made of the same material as gear 44. The housing 34, shaft 40 and gears 42, 44 may be made from a very hard, rugged durable synthetic material which has good wear characteristics, such as acetal, Deltran (a nylon material), polycarbonate (such as Noryl or Lexan) or other sufficiently hard or reinforced plastic (i.e., reinforced with glass fibers, graphite fibers, or other suitable material) suitable for use in the mouth and approved by the FDA. Metal, however, is preferring for housing 34, shaft 40 and gears 42, 44 to produce the best performance, durability, operability, and autoclaveability when the drive means 34, 40, 42 is to be re-used a plurality of times.

Figures 5, 6:
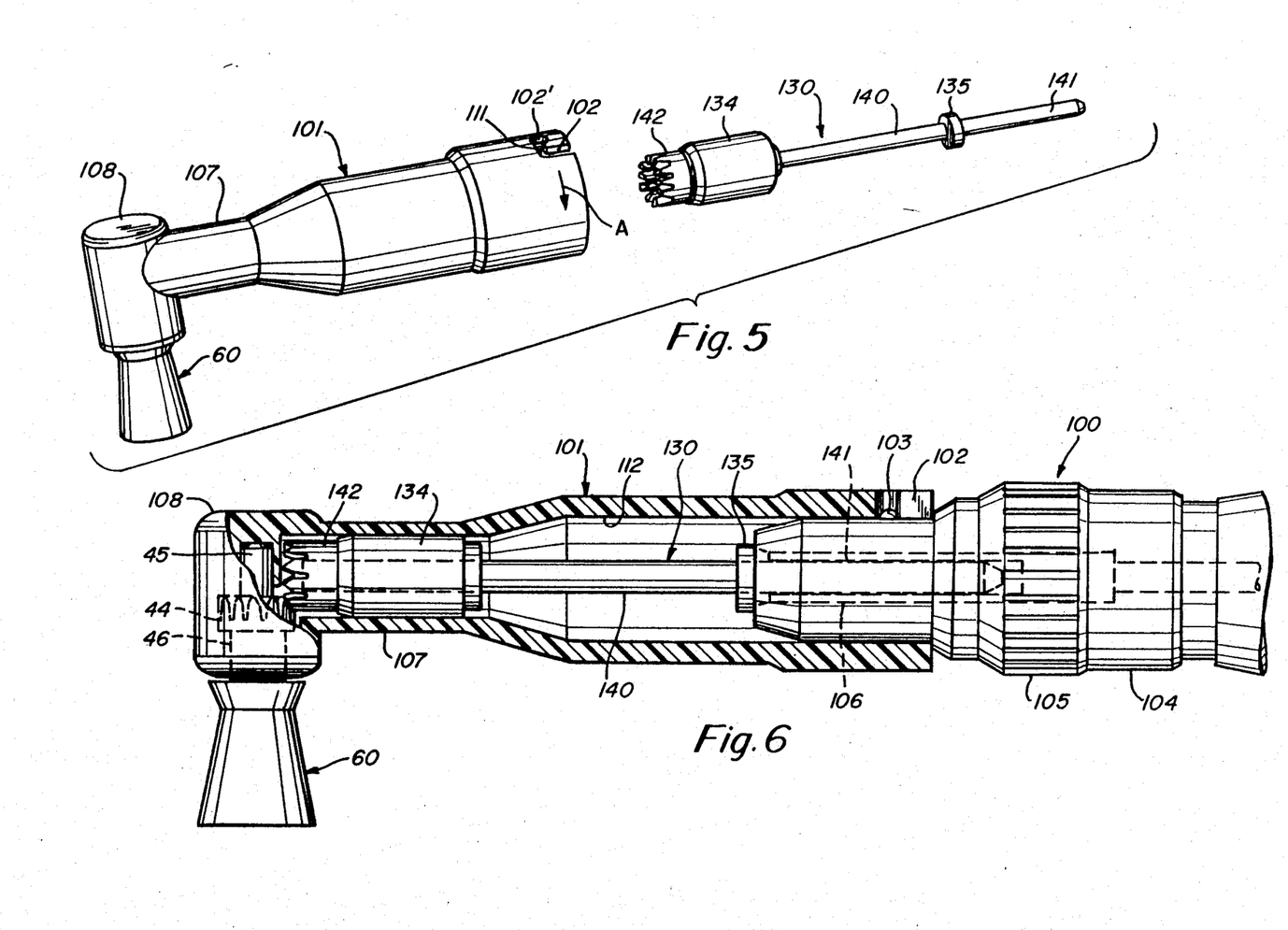
FIG. 5 is a disassembled perspective view of a modified embodiment of the present invention.
FIG. 6 is a longitudinal cross-sectional view of the embodiment of FIG. 5, in the assembled state.

Referring to FIGS. 5 and 6, a modified embodiment of the right angle dental handpiece of the present invention is shown. In FIGS. 5 and 6, elements which are the same as in FIGS. 1 and 2 are given the same reference numerals, and are not further described, since their structure and function are essentially the same as previously described with respect to FIGS. 1 and 2.

In the embodiment of FIGS. 5 and 6, the disposable hollow outer plastic housing 101 has a bayonet slot 102 formed at the proximal end thereof for interconnection with a projection 103 on the drive portion 100 of the dental hand tool The bayonet slot 102 has a rearwardly curved recess portion 102 for snappingly receiving the projection 103 therein through the slightly reduced opening area 111. The snapping engagement is due to the resiliency of the plastic of housing 101 as the projection is forced past the opening 111 when turning housing 101 during installation. The dental hand tool 100 is of conventional design and has a chuck portion 104, a jaw release knob 105 and gripping jaws 106, which will be described hereinafter.

As mentioned above, the outer housing 101, which is essentially similar to the outer housing 10 of FIGS. 1 and 2, is preferably made of plastic material and is disposable. The drive member 130 is mounted therein (as will be described below) is preferably made of metallic material, such as brass, so that it can be re-used or disposed of after each use. Alternatively, the drive member 130 can be made of a hard, durable plastic material, or other suitable material, which can be re-used (after sterilization, for example) and/or disposed of, as desired. The design of the drive member 130 is relatively simple and inexpensive to manufacture. Therefore, even if it is disposed of often, the design is still economical.

The outer plastic housing 101 has an inner elongated opening 112 formed therein for receiving the drive member 130. The drive member 130 comprises a shaft portion 140 which extends in the longitudinal direction thereof. The drive member 130 is rotatable about the longitudinal axis of the shaft portion 140. The drive member 130 also comprises a bearing portion 134 at the forward portion thereof which is mounted in the necked-down portion 107 of the housing 101 so as to serve as a bearing and front support member to provided good rotational characteristics to the drive member 130 when mounted in the housing 101. The drive member 130 also has a gear 142 at the distal end thereof which meshes with gear 44, which imparts rotation to the cup 60 in the same manner as in the previously described embodiments of FIGS. 1 and 2. The drive member 130 also has a depth stop member 135 thereon which, when the apparatus is assembled, bears on the forward end of the dental drive tool 100 to maintain the drive member 130 in its proper position within the housing 101. The depth stop 135 maintains proper engagement of the gears 142 and 44, to insure proper operation of the apparatus in use.

To use the apparatus of FIGS. 5 and 6, first the drive member 130 is mounted in the gripping jaws 106 of the prior art drive tool for example by turning jaw release knob 105 (as is conventional) to release the jaws 106, inserting the proximal end portion 141 of the drive member 130 into the opening defined by the jaws 106 (as shown in FIG. 6), and then releasing or turning the jaw release knob 105 to tighten the jaws 106 on said proximal end portion 141 of the drive member 130. In this position, the depth stop 135 is adjacent the distal end of the dental drive tool to properly the orient the members relative to each other, as shown in FIG. 6. Then, the housing 101 (with the drive cup and gear 44 assembly preassembled therein) is mounted over the drive member 130 and is locked onto the dental drive tool by means of the bayonet opening 102 which engages with the projection 103 on the dental drive tool. This is accomplished by placing the housing 101 over the dental drive tool so that the projection enters into the open end of bayonet opening 102, and then twisting the outer housing 101 relative to the dental drive tool in the direction of the arrow A shown in FIG. 5. This locks all of the members relative to each other and provides an assembly having a high degree of structural integrity. It is critical that the housing 101 be locked relative to the dental drive member 100 in the longitudinal direction to prevent longitudinal relative movement. This maintains the gears 142 and 44 in proper engagement for proper driving of the cup 60. The depth stop 135 also cooperates with the drive tool 100 to maintain the members in proper orientation during use. The bearing portion 134 provides support at the forward or distal end, whereas the shaft portion 141 engaged in the gripping jaws 106 provide support at the proximal end, thereby providing an overall device having very good operational characteristics in use.

The device of FIGS. 5 and 6 in some instances is preferable since the drive member 140 is simpler in construction than the drive member 30 of FIGS. 1 and 2. As mentioned hereinabove, the drive member 130 can be fabricated of a metallic material such as brass, so that it has a very long, useful life, and can be re-used after sterilization, if desired. Since the drive member 130 is interior of the housing, and does not get exposed to contamination, it can be even re-used with minimal cleaning after a first use.

Figure 7:
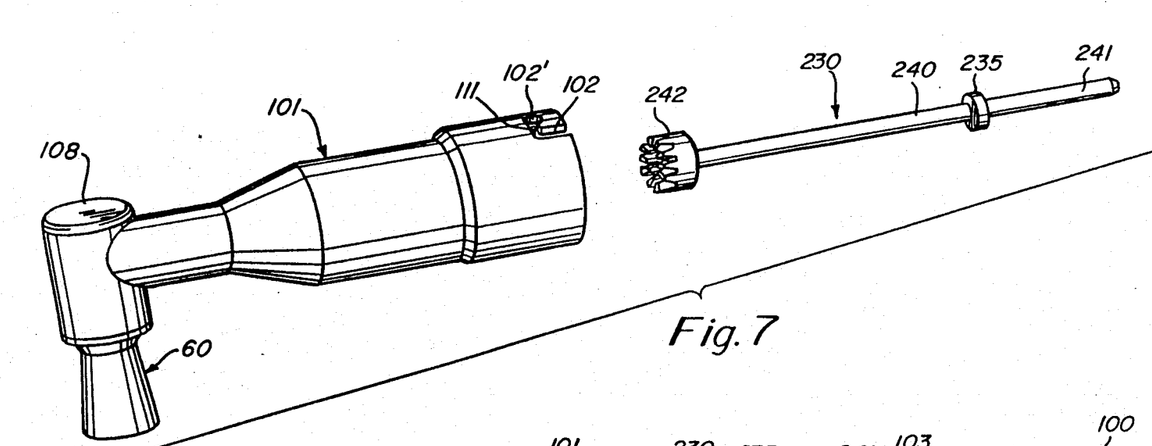
FIG. 7 is a disassembled perspective view of a further modified embodiment of the present invention.
Figure 8:
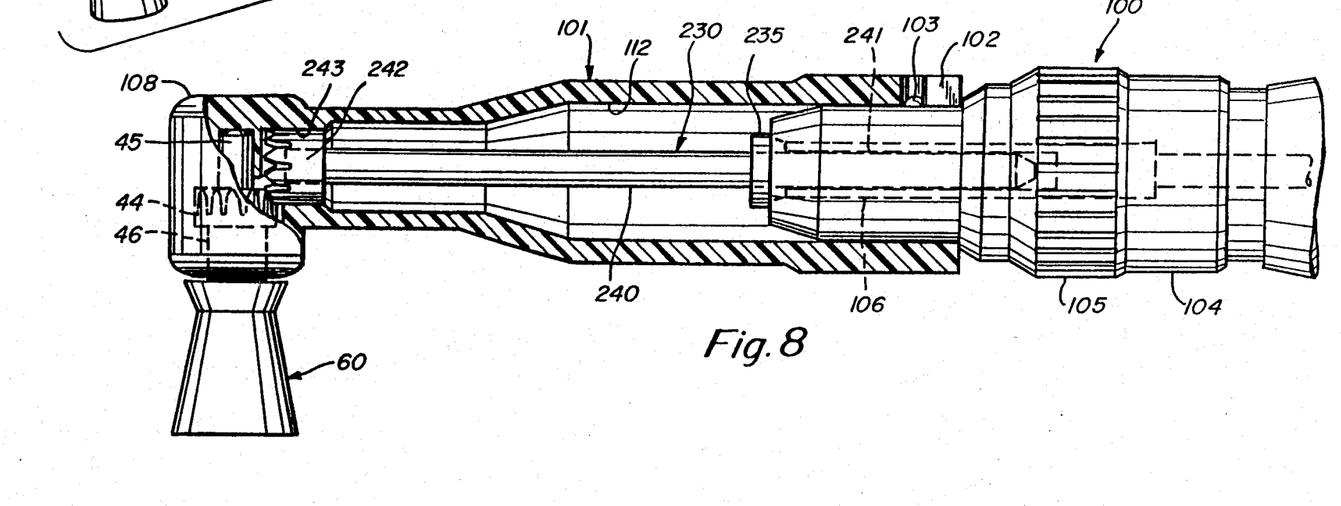
FIG. 8 is a longitudinal cross-sectional view of the embodiment of FIG. 7, in the assembled state.

FIGS. 7 and 8 illustrate a further modified embodiment of the invention. In FIGS. 7 and 8 the housing 101 is the same as the housing 101 shown in FIGS. 5 and 6. Therefore, a further detailed description thereof is omitted.

In the embodiment of FIGS. 7 and 8, the drive member 130 is replaced by a modified drive member 230 which has a shaft portion 240, and depth stop 235, which function the same as in the embodiment of FIGS. 5 and 6. The proximal end portion 241 of the shaft is engaged in the gripping jaws 106 of the drive tool 100 in the same as previously described with respect to FIGS. 5 and 6. In the embodiment of FIGS. 7 and 8, the bearing and support portion 134 of the drive member 130 is omitted, and instead, the gear 242 has an outer surface thereon which serves as a support and a bearing with the internal surface of the distal end portion of the housing 101, as shown in FIG. 8. As seen in FIG. 8, the distal end portion of the housing 101 has an inner surface 243 against which said bearing portion 242 rotatably bears. Operationally, the apparatus of FIGS. 7 and 8 operates and functions essentially similar to the apparatus of FIGS. 5 and 6 and is assembled in substantially the same manner. Therefore, a further detailed discussion of FIGS. 7 and 8 is omitted.

Figure 9:
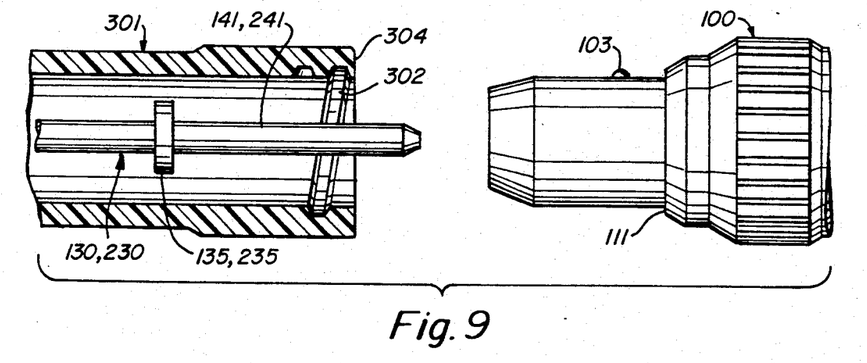
FIG. 9 is a partially broken view showing an interconnection between the members of a disposable dental handpiece and the dental drive tool.

FIG. 9 illustrates a modified arrangement for interconnecting the housing 301 (which is essentially similar to the housings 101 and 201) to the dental drive tool 100. The dental drive tool 100 has a projection 103 on the outer circumference of the distal end portion thereof, as discussed above with respect to FIGS. 5-8. Instead of the housing member 101, 201 having a bayonet opening 102 for engaging the projection 103, a threaded portion 302 is provided internally of the end of the housing member 301 for threadably engaging the projection 103. The housing 301 is installed on the dental drive unit 100 after the drive member 130, 230 is installed in the dental drive unit 100. The housing 301 is placed over the distal end of the drive device 100 and the thread 302 is threaded onto the projection 103 until the end of the thread 302, or until the end surface 304 of the housing 301 abuts against end surface 111 of drive device 100. This orients the members in the proper longitudinal positions, and maintains them in their proper longitudinal positions so that the gear drive mechanism for the cup 60 remains positively engaged and provides good operational characteristics in use.

Figure 10:
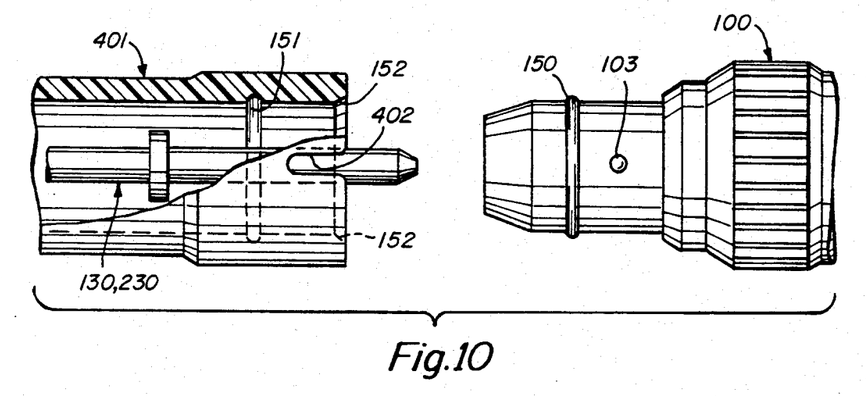
FIG. 10 is a partially broken view showing another interconnection between the members of a disposable dental handpiece and the dental drive tool.

FIG. 10 illustrates a further modified embodiment wherein the drive member 130, 230 is the same as shown in FIG. 9 (that is, is either the embodiment of FIGS. 5-6 or FIGS. 7-8). The housing 401 is essentially similar to the housing 101, except for the interconnection portion at the end thereof which interconnects with dental drive member 100. In the embodiment of FIG. 10, the dental drive member 100 has a projection 103 thereon which engages in a longitudinal anti-rotation slot 402 formed in the end of the housing 401. The slot 402 and projection 103 prevent rotation of the housing 401 about the longitudinal axis of the device after engagement with the dental drive unit. In order to prevent longitudinal movement after mounting of the housing on the drive unit 100, the drive unit 100 is provided with a circumferential ridge or projection 150 which engages into a circumferential groove 151 formed in the internal surface of the open end portion of the housing member 401. The open end of the housing member 401 has an inclined lead-in surface 152 which facilitates insertion of the housing member 40 over the drive member 100. As in the above embodiments, first the drive member 130, 230 is mounted on the end of the drive device 100. Then, the housing member 401 is inserted thereover, and is pressed onto the free end of the drive device 100 with the slot 402 engaged with the projection 103. The inclined lead-in surface 152 facilitates passing the plastic outer housing 401 over the circumferential projection 150. Due to the inherent resiliency of the plastic of the disposable plastic outer housing 401, the outer housing may be frictionally pressed over the circumferential projection 150 until it "snaps" into the inner circumferential groove 151 formed internally of the housing member 401. Upon snapping engagement of the projection 150 into the groove 151, the housing member 401 is locked longitudinally to prevent inadvertent and undesired longitudinal movement relative to the drive device 100 during use. To remove the housing 401 from the drive device 100, a pull-out force is manually applied to the outer housing 401 to disengage the housing 401 from the drive tool 100. This is accomplished because of the inherent resiliency of the plastic material of the outer housing 401.

Figure 11:
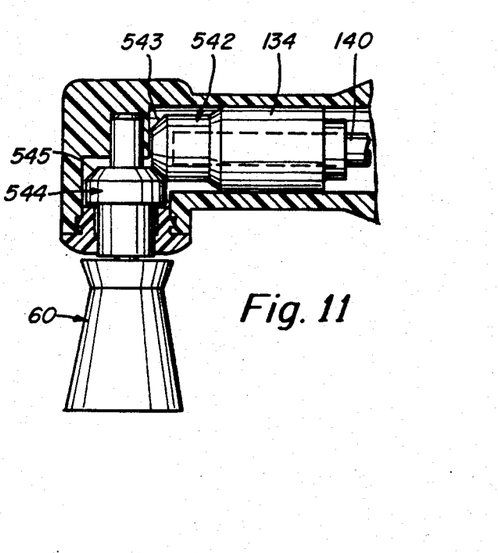
FIG. 11 shows a modified embodiment of the distal end of the disposable dental handpiece of the present invention, using friction drive and driven members.

FIG. 11 illustrates a modified embodiment wherein the gears 44, 42 (142, 242) are replaced by frictional drive elements 544, 542, respectively. The frictional drive elements 544, 542 preferably have inclined surfaces 545, 543 which bear on each other during use, and which are in frictional engagement. The remainder of the device is substantially the same as any of the embodiments described hereinbefore. Upon rotation of the shaft 140, to which friction engagement member 542 is fixedly attached, the member 542 rotates and the inclined frictional engagement surface 543 drive member 54 via its inclined frictional engagement 545, to thereby drive the cup 60 in the same manner as previously described with the other embodiments. As should be clear, the frictional engagement members 544, 542 can replace any of the gear members shown in any of the other embodiments, as desired. The embodiment shown in FIG. 11 is shown only by way of example, but any of the other illustrated embodiments may be readily modified by replacing the gears with the frictional engagement members.

Figure 12:
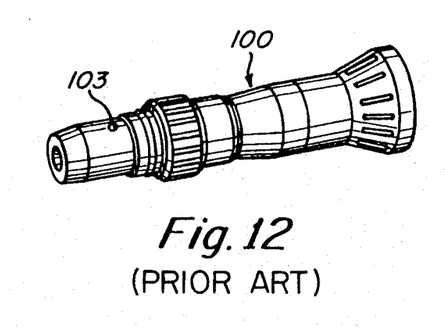
FIG. 12 is a perspective view of a prior art dental drive handpiece.

FIG. 12 shows a prior art drive device 100 which is usable with the embodiments described hereinabove. This device is conventional and need not be further described.

Figure 13:
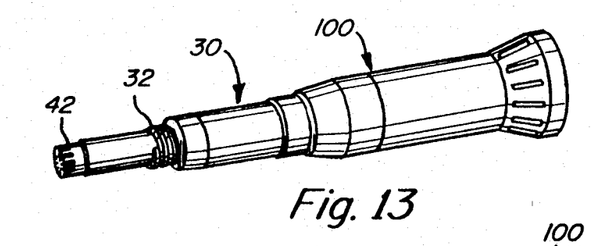
FIG. 13 is a perspective view of a further modified embodiment of the present invention.

FIG. 13 is a modification of the embodiment of FIG. 12, wherein the dental drive tool 100 has a modified forward end which includes a drive housing similar to that shown in FIGS. 1 and 2. For the embodiment of FIG. 13, in order to show correspondence of elements, like reference numerals as used in FIGS. 1 and 2 are used in FIGS. 13 and 14 which shows an enlarged longitudinal cross-sectional view of the embodiment of FIG. 13. FIG. 15 shows an arrangement similar to FIG. 13, but where the device is configured as a contra-angle device, details of which are not described herein. A contra-angle of about 15° is preferred, but any desired angle could be used. The contra-angle dental driving tool can be used with any of the embodiments of the invention, as should be readily apparent.

As seen in FIG. 13, the drive member 30 is integrally formed with the drive device 100, and use thereof is similar to use of the embodiment of FIG. 1, except that the drive member 30 is permanently attached to the dental drive tool 100. The dental drive tool 100 is connected to the dental apparatus, and then the outer housing 10 of FIG. 1 is threadably mounted over the drive member 30 and the internal threads 14 of the embodiment of FIG. 1 are engaged with the outer threads 32, to fixedly engage the outer housing 10 over the drive member 30 of the embodiment of FIG. 13. In this position, the gear 42 is driving engaged with the gear 44, which in turns drives the cup 60, as in the embodiment of FIGS. 1 and 2.

Figure 14:
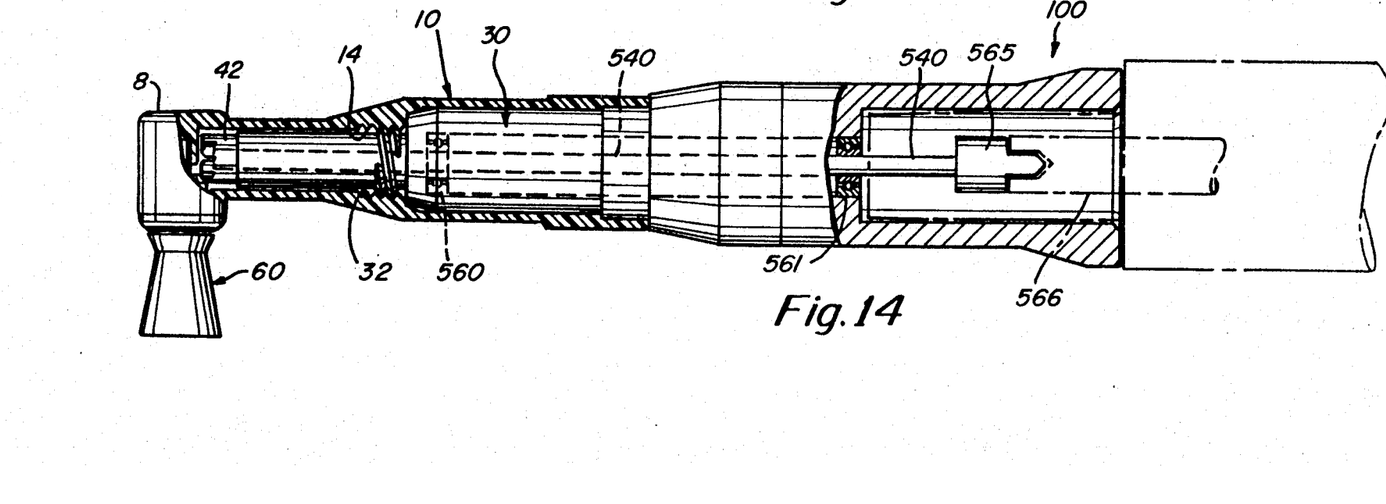
FIG. 14 is a longitudinal cross-sectional view of the embodiment of FIG. 12, in the assembled state.
Figure 15:
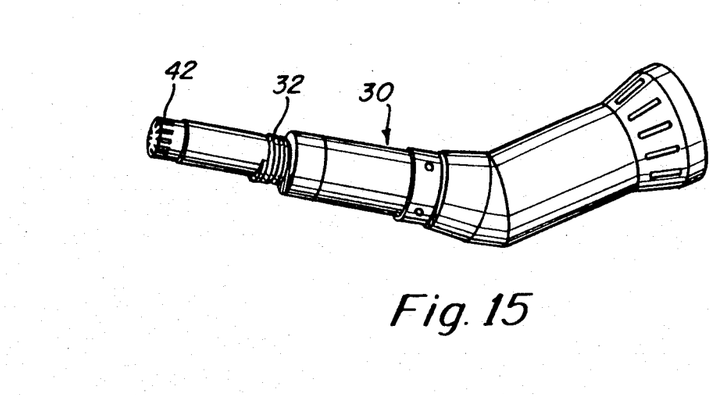
FIG. 15 is a perspective view, similar to that of FIG. 13, of a contra-angle embodiment of the present invention, the internal details of which are similar to those shown in FIG. 14.

FIG. 14 shows in greater detail how, for example, the drive member 30 is attached to the dental tool 100. Bearings 560, 561 may be provided for rotatably supporting the shaft portion 540 of drive member 30, as shown in FIG. 14. The bearings may be conventional ball bearings, sleeve bearings or any other type of inexpensive bearing (such as bearing 41 in FIG. 2). The remote end of shaft 540 carries a drive shaft connector 565 which engages with a member 566 of the prior art-type drive member 100.

The drive connection between members 565 and 566 is accomplished via a jaw-type chuck, or other suitable connection device, as is accomplished in the prior art.

While the embodiment of FIGS. 13 and 14 has been shown as comprising a drive device 30 similar to that of FIGS. 1 and 2, it should be clear that other drive members, such as drive member 130 of FIGS. 5 and 6 and drive member 230 of FIGS. 7 and 8, could be used instead. In such a case, instead of threading of the outer housing 10 onto the drive member 30 as shown in FIG. 14, the interconnecting techniques of FIGS. 5-8 (and also FIGS. 9 and 10), for example would be used, as required for the particular application. The critical factor here is that the drive member 30, 130, 230, etc. is attached as a unit to the dental drive tool 100 and the outer housing is merely replaced as required. In such a case, a special dental drive tool 100 is provided with the appropriate drive member 30, 130, 230 connected at the end thereof, onto which a disposable outer housing is removably attached.

Figure 16:
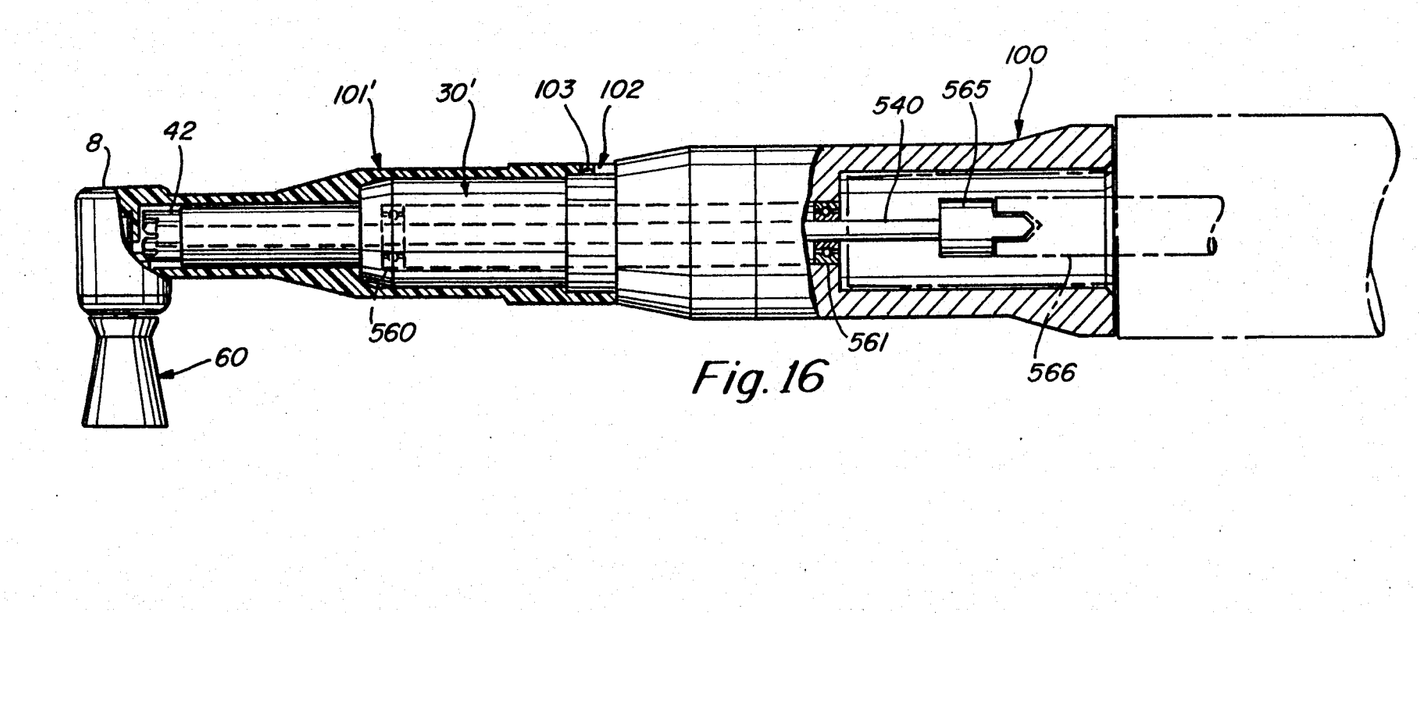
FIG. 16 is a longitudinal cross-sectional view of an embodiment similar to that of FIG. 14, but with a different interconnection mechanism for interconnecting the outer housing to the dental tool.

FIG. 16 shows a configuration along the lines set forth in the paragraph immediately above. In FIG. 16, the drive member 30' is similar to the drive member 30 of FIG. 14, except that the threads 32 thereof are omitted. The housing member 101' of FIG. 16 is similar to the housing 101 of FIG. 5, described hereinabove, except that it is configured to receive the drive member 30' therein. The housing 101' of FIG. 16 has, for example, a bayonet opening 102 which is identical to the bayonet opening 102 shown in FIG. 5. The projection 103 of the drive unit is engageable in the bayonet 102 to lock the housing 101' both longitudinally and circumferentially in place relative to the drive unit. As should be clear, the drive member 30' may be replaced with any of the other drive members, for example 130, 230, etc. shown herein, and the outer housing can be suitably configured to receive same. Also, instead of the bayonet interconnection shown in FIG. 16, any of the other interconnections shown and described herein can be used for locking the outer housing both longitudinally and circumferentially relative to the dental drive tool 100. The showing in FIG. 16 is merely by way of example, and is exemplary.

Figure 17:
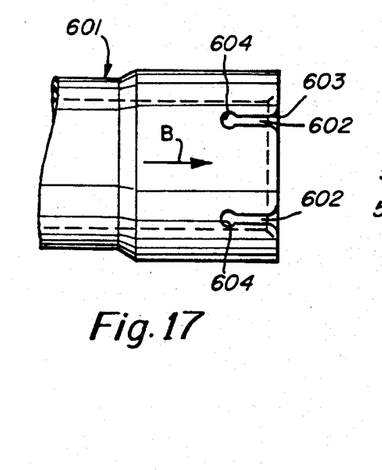
FIG. 17 is a partial view of an outer housing showing a modified engagement mechanism for connecting same to a dental tool.

FIG. 17 illustrates another interconnection technique for interconnecting a housing member 601 to a dental drive tool 100. In the embodiment of FIG. 17, the partially shown housing member 601 has anti-rotational slots 602 formed therein which receive a projection 103 of the dental drive tool 100 in a manner similar to the anti-rotational slot 402 shown in FIG. 10. The slots 602 have rounded lead-in opening ends 603 to facilitate insertion over a projection 103. The projection 103 and the slots 602 are dimensioned so that projection 103 frictionally engages the side wall of slots 602 during insertion. The housing 601 is continued to be pressed in the direction of the arrow B in FIG. 17 onto a dental drive tool 100, and the projection 103 then passes into the enlarged inner opening 604 of the slots 602 so as to "lock" in place. The projection 103 essentially "snaps" into the enlarged opening 604 after frictionally passing through the side walls of slots 602, due to the resiliency of the plastic material of the housing member 601. This configuration locks the housing member 601 in the longitudinal direction (due to the frictional fit of the projection 103 with the side walls of slot 602) and also locks the housing 601 circumferentially relative to the drive tool 100. Preferably, a plurality of slots 602 are provided around the circumference of housing member 601 (preferably three such slots are provided, for example) so that the housing 601 can be attached to the dental drive tool 100 at different angular orientations, to facilitate use by a dentist, as desired. This type of arrangement is particularly useful with a contra-angle dental drive tool 100 to enable the practitioner to reach hard-to-get-at portions within the mouth of a patient.

The various interconnection mechanisms between the disposable outer housing and the dental driving tool ca be used in any combination with appropriate re-usable drive shaft means, as should be apparent from the various drawings which show specific, but not limiting, embodiments.

While the invention has been described above with respect to specific embodiments, various modifications and alterations can be made within the scope of the invention a defined by the appended claims.

What is claimed is:

1. A disposable dental handpiece comprising:
a one-piece disposable outer housing made of a disposable plastic material and having an elongated opening therein for receiving a drive shaft means, said one-piece outer housing being disposable after use thereof;
a cavity in said one-piece outer housing for receiving a driven rotatable member;
means for coupling a working member to said driven member for performing a working operation in an oral cavity of a patient;
a re-usable drive shaft means removably mounted in said elongated opening in said one-piece outer housing, said re-usable drive shaft means including:
a rotatable drive shaft removably receivable in said one-piece outer housing and being rotatable relative to said one-piece outer housing, said drive shaft being drivingly coupled at one end portion thereof to a dental drive means of a dental tool, so as to be rotatably driven by said dental drive means within said one-piece outer housing; and
a rotatable driving member at a distal end portion of said drive shaft, which distal end portion is opposite from said one end portion thereof, for engaging with said driven member and for rotatably driving said driven member; and
releasable connecting means including:
first connecting means for removably coupling said one-piece outer housing over said re-usable drive shaft means and for fixing said re-usable drive shaft means to prevent one-piece outer housing to substantially prevent relative movement therebetween in an axial direction of said drive shaft during use; and second connecting means removably connecting said one-piece outer housing to said dental drive means of said dental tool such that said driving member is in engagement with said driven member during use, said second connecting drive means including means for fixing said one-piece outer housing to said dental drive means so as to positively prevent both longitudinal and circumferential movement of said one-piece outer housing relative to said dental drive means during use;

said first and second connecting means permitting easy and quick disengagement of said one-piece outer housing from both said dental drive means and from said re-usable drive shaft means;

said re-usable drive shaft means being releasably disconnectable from and removable from said one-piece outer housing, when released, for disposable of said one-piece outer housing without disassembly or breaking of said one-piece outer housing.

2. The dental handpiece of claim 1, wherein said outer housing comprises a portion which is engageable over an end portion of said dental drive means, said dental drive means having a projection thereon, and wherein said second connecting means comprises a bayonet opening in said portion of said outer housing which is engageable over said dental drive means for lockingly receiving said projection of said dental drive means.

3. The dental handpiece of claim 1, wherein said second connecting means comprises a threaded portion at the end of said outer housing adjacent the opening portion of said elongated opening, and wherein said dental drive means includes means for threadably engaging said threaded portion.

4. The dental handpiece of claim 1, wherein:
said dental drive means comprises first and second projections thereon; and
said second connecting means comprises a non-rotational opening on said outer housing for non-rotationally engaging one of said projections, and an internal recess in said outer housing for engaging said second projection for preventing longitudinal movement of said outer housing relative to said dental drive means.

5. The dental handpiece of claim 4, wherein said second projection snappingly engages within said recess of said outer housing due to the resiliency of the material of said outer housing.

6. The dental handpiece of claim 1, wherein said driving member and said driven member comprise frictional engaging means for providing frictional engagement therebetween.

7. The dental handpiece of claim 1, wherein said re-usable drive shaft means is made of metallic material which is sterilizable for re-use.

8. The dental handpiece of claim 1, wherein said re-usable drive shaft means comprises a bearing member thereon for bearing against said inner surface of said outer housing to serve as a bearing and rotational support member for said drive shaft means within said outer housing.

9. The dental handpiece of claim 1, wherein said re-usable drive shaft means further comprises an end stop member thereon for bearing against an end surface of said dental driving tool to locate said drive shaft means relative to said dental driving tool and said outer housing to provide engagement between said driving and driven members.

10. A disposable dental handpiece unit, comprising:
a one-piece disposable outer housing made of a disposable plastic material and having an elongated opening therein for receiving a drive shaft means, said outer housing being disposable after use thereof;
a cavity in said outer housing for receiving a driven rotatable member;
means for coupling a working member to said driven member for performing a working operation in an oral cavity of a patient;
a re-usable drive shaft means removably mounted in said elongated opening in said one-piece outer housing, said re-usable drive shaft means including:
a rotatable drive shaft in said one-piece outer housing and being rotatable relative to said one-piece outer housing, said drive shaft being driven at one end portion thereof by a dental drive means of a dental tool, so as to be rotatably driven within said one-piece outer housing;
an intermediate member interposed between said one-piece outer housing and said drive shaft, and bearing on an inner surface portion of said one-piece outer housing, said intermediate member encircling said drive shaft over at least a portion of the length of said drive shaft and supporting at least a portion of said drive shaft, said drive shaft being rotatable relative to said intermediate member; and
a driving member at a distal end portion of said drive shaft, which distal end portion is opposite from said one end portion thereof, for engaging with and rotatably driving said rotatable driven member; and
releasable engaging means for removably coupling said re-usable drive shaft means to said one-piece outer housing for removably securing said re-usable drive shaft means in said elongated opening of said one-piece outer housing with said re-usable drive shaft means being substantially immovable relative to said one-piece outer housing in the axial direction thereof when in use, such that said driving member is in engagement with said driven member during use, and for permitting quick and easy disengagement of said re-usable drive shaft means from said outer housing for disposal of said one-piece outer housing;
said releasable engaging means including:
first connecting means for removably coupling said one-piece outer housing to said intermediate member of said re-usable drive shaft means for thereby fixing said one-piece outer housing over said re-usable drive shaft means to substantially prevent relative movement therebetween in both axial and circumferential directions of said drive shaft; and
second connecting means removably connecting said one-piece outer housing to said dental drive means of said dental tool, said second connecting drive means including means for fixing said one-piece outer housing to said dental drive means so as to positively prevent both longitudinal and circumferential movement of said one-piece outer housing relative to said dental drive means, said first and second connecting means permitting easy and quick disengagement of said one-piece outer housing from both said dental drive means and from said re-usable drive shaft means, said re-usable drive shaft means being releasable from and removable from said one-piece outer housing, when released, without disassembly or breaking of said one-piece outer housing for disposal of said one-piece outer housing.

11. A disposable dental handpiece comprising:

a disposable outer housing made of a disposable plastic material and having an elongated opening therein for receiving a drive shaft means, said outer housing being disposable after use thereof;

a cavity in said outer housing for receiving a driven rotatable member;

means for coupling a working member to said driven member for performing a working operation in an oral cavity of a patient;

a re-usable drive shaft means removably mountable in said elongated opening in said outer housing, said re-usable drive shaft means including:

a rotatable drive shaft removably receivable in said outer housing and being rotatable relative to said outer housing, said drive shaft being drivingly coupled at one end portion thereof to a dental drive means of a dental tool, so as to be rotatably driven by said dental drive means within said outer housing; and a rotatable driving member at a distal end portion of said drive shaft, which distal end portion is opposite from said one end portion thereof, for engaging with said driven member and for rotatably driving said driven member; and releasable connecting means for removably coupling said outer housing over said re-usable drive shaft means and for removably connecting said outer housing to said dental drive means of said dental tool such that said driving member is in engagement with said driven member during use, said connecting means including means for fixing said outer housing to said dental drive means so as to positively prevent both longitudinal and circumferential movement of said outer housing relative to said dental drive means and for substantially preventing longitudinal movement of said re-usable drive shaft means relative to said outer housing, and for permitting easy and quick disengagement of said outer housing from both said dental drive means and from said re-usable drive shaft means;

said releasable connecting means including: first and second projections on said dental drive means; and a non-rotational opening on said outer housing for non-rotationally engaging one of said projections, and an internal recess in said outer housing for engaging said second projection for preventing longitudinal movement of said outer housing relative to said dental drive means; and said re-usable drive shaft means being releasably disconnectable from and removable from said outer housing, when released, for disposal of said outer housing without disassembly or breaking of said outer housing.

12. The dental handpiece of claim 11, wherein said second projection snappingly engages within said internal recess of said outer housing due to resiliency of the material of said outer housing.

* * * * *